United States Patent [19]

Menapace

[11] 4,188,348
[45] Feb. 12, 1980

[54] HYDROGENATION OF CYCLOPENTADIENE TO FORM CYCLOPENTENE

[75] Inventor: Henry R. Menapace, Stow, Ohio

[73] Assignee: The Goodyear Tire & Rubber Company, Akron, Ohio

[21] Appl. No.: 932,874

[22] Filed: Aug. 11, 1978

[51] Int. Cl.$^2$ ............... C07C 5/06; C07C 5/14; C07C 5/16

[52] U.S. Cl. .................................. 585/274

[58] Field of Search .................... 260/666 A

[56] References Cited

U.S. PATENT DOCUMENTS

| | | | |
|---|---|---|---|
| 3,855,327 | 12/1974 | Billings | 260/666 A |
| 3,890,400 | 6/1975 | La Grange et al. | 260/666 A |
| 3,937,745 | 2/1976 | Wideman et al. | 260/666 A |
| 4,108,911 | 8/1978 | Wideman et al. | 260/666 A |

*Primary Examiner*—Veronica O'Keefe

[57] ABSTRACT

There is disclosed an improved process for selectively hydrogenating cyclopentadiene to form cyclopentene in the presence of a catalyst comprising (A) a hydrocarbon-soluble nickel compound such as nickel salts of carboxylic acids or organo nickel compounds, (B) an organo reducing agent such as organoaluminum compounds or lithium alkyl compounds and (C) pyridine, the improvement being that the soluble nickel compound and the pyridine are employed in amounts wherein the mole ratio of aluminum or lithium to the nickel ranges from 7/1 to 11/1 and the mole ratio of the pyridine to the nickel compound ranges from 1/1 to 2.5/1.

3 Claims, No Drawings

HYDROGENATION OF CYCLOPENTADIENE TO FORM CYCLOPENTENE

BACKGROUND OF THE INVENTION

In German Pat. No. 2,327,230 there is disclosed a process for the selective hydrogenation of unsaturated hydrocarbons, particularly cyclopentadiene to form cyclopentene, whereby hydrogen is reacted with the unsaturated hydrocarbons in the presence of a catalyst containing an organic nickel derivative and a reducing agent characterized in that the reducing agent corresponds to the formula Al $R_1$ $R_2$ $R_3$ or to the formula R-Li where $R_1$, $R_2$ and $R_3$ are hydrogen or monovalent hydrocarbon radicals and R is a monovalent hydrocarbon radical and the operation is conducted in the presence of pyridine.

In this German patent it is said that maximum catalyst activity is advantageously produced by observing the following conditions. The mole ratio between the aluminum or lithium compound and the nickel salt can lie between 2.6/1 and 4/1 but normally a mole ratio of 3/1 is employed. The ratio between the pyridine and the nickel salt can lie between 1/1 and 2.5/1, but normally a ratio of 2/1 is employed. It is said that the temperature of catalyst preparation and the hydrogenation temperature can lie between 0 and 100° C., but, generally, the catalyst is prepared between 10 and 50° C. The hydrogenation generally takes place between 0 and 80° C.

A number of examples are given in this German Patent. For instance, it is disclosed that into a reaction vessel, from which air and moisture have been removed, are introduced 300 milliliters (ml) of freshly prepared cyclopentadiene (CPD) and then the catalyst solution made by reacting 0.9 millimoles (mm) of triethylaluminum in benzene with a solution of 0.3 mm of nickel acetylacetonate in benzene which contains 0.6 mm of pyridine. The reaction is conducted at 30° C. under hydrogen pressure of 30 bars. After a certain period of time, the reaction was stopped.

The applicant has set forth a number of experimental conditions, times and results of several of the experiments which were conducted and are reported in this German Patent. These experiments are set forth in the table below:

Table 1

| Ex No | Al/Ni Mole Ratio | Time Min. | Conv. of CPD | % Cyclopentane Obtained | % Cyclopentene Obtained |
|---|---|---|---|---|---|
| 7 | 1.0 | 150 | 100 | 4 | 94 |
| 8 | 2.6 | 80 | 100 | 4 | 96 |
| 1 | 3.0 | 72 | 100 | 4 | 96 |
| 9 | 4.0 | 75 | 100 | 4 | 96 |
| 10 | 6.0 | 80 | 100 | 8 | 92 |

What is particularly important here are the times employed in the hydrogenations of the table above. These times give an indication of the rate of the hydrogenations.

SUMMARY OF THE INVENTION

The applicant has found that by the expedient of shifting the aluminum or lithium to nickel mole ratio of 2.6/1 to 4/1 disclosed in the German Patent to a new range from 7/1 to 11/1, that an unexpected improvement can be obtained in the rate of hydrogenation of cyclopentadiene. This is double the rate obtained by the patentees of German Pat. No. 2,327,230.

Thus, the invention is an improvement in the process of hydrogenation of cyclopentadiene (CPD) to form cyclopentene (CPE). The invention is described as follows:

In the process of selectively hydrogenating cyclopentadiene to form cyclopetene in the presence of a catalyst comprising (A) a hydrocarbon-soluble nickel compound selected from nickel salts of carboxylic acids or organonickel compounds, (B) organo reducing agent corresponding to the formula Al $R_1$ $R_2$ $R_3$ wherein $R_1$ is a monovalent hydrocarbon radical or hydrogen and $R_2$ and $R_3$ are monovalent hydrocarbon radicals, or to the formula R-Li where R is a monovalent hydrocarbon radical, and (C) pyridine, the improvement comprising employing the organo reducing agent and the soluble nickel compound in amounts wherein the mole ratio of aluminum or lithium to nickel ranges from 7/1 to 11/1.

DETAILED DESCRIPTION

The (A) component of the catalyst of this invention which contains nickel may be any organo nickel compound which is a soluble compound of nickel. These soluble nickel compounds are normally compounds of nickel with a mono- or bi-dentate organic ligand containing up to 20 carbon atoms. "Ligand" is defined as an ion or molecule bound to and considered bonded to a metal atom or ion. Mono-dentate means having one position through which covalent or coordinate bonds with the metal may be formed; bi-dentate means having two positions through which covalent or coordinate bonds with the metal may be formed. By the term "soluble" is meant soluble in inert solvents. Thus, any salt or an organic acid containing from about 1 to 20 carbon atoms may be employed. Representative of organo nickel compounds are nickel benzoate, nickel acetate, nickel naphthenate, nickel octanoate, bis(α-furyl dioxime)nickel, nickel palmitate, nickel stearate, nickel acetylacetonate, nickel salicaldehyde, bis(cyclopentadiene) nickel, bis(salicylaldehyde)ethylene diimine nickel, cyclopentadienyl-nickel nitrosyl, bis(π- allyl nickel trifluoroacetate), and nickel tetracarbonyl. The preferred component containing nickel is a nickel salt of a carboxylic acid or an organic complex compound of nickel. The most preferred are 2-ethyl hexanoate, per-decanoate and the naphthenate salts of nickel. The (B) component is an organoaluminum compound. By the term "organoaluminum compound" is meant any organoaluminum compound responding to the formula:

in which $R_1$ is selected from the group consisting of alkyl (including cycloalkyl), aryl, alkaryl, arylalkyl, alkoxy and hydrogen; $R_2$ and $R_3$ being selected from the group of alkyl (including cycloalkyl), aryl, alkaryl, and arylalkyl. Representative of the compounds responding to the formula set forth above are: diethyl aluminum hydride, di-n-propyl aluminum hydride, di-n-butyl aluminum hydride, diisobutyl aluminum hydride, diphenyl aluminum hydride, di-p-tolyl aluminum hydride, dibenzyl aluminum hydride, phenyl ethyl aluminum hydride, phenyl-n-propyl aluminum hydride, p-tolyl ethyl aluminum hydride, p-tolyl n-propyl aluminum hydride, p-tolyl isopropyl aluminum hydride, benzyl ethyl aluminum hydride, benzyl n-propyl aluminum hydride, and benzyl isopropyl aluminum hydride and other organoaluminum hydrides. Also, diethylaluminum ethoxide, diisobutylaluminum ethoxide, and dipropylaluminum methoxide. Also included are trimethyl aluminum, triethylaluminum, tri-n-propyl aluminum, triisopropylaluminum, tri-n-butylaluminum, triisobutylaluminum, tripentylaluminum, trihexylaluminum, tricyclohexylaluminum, trioctylaluminum, triphenyl aluminum, tri-p-tolylaluminum, tribenzylaluminum, ethyl diphenylaluminum, ethyl di-p-tolylaluminum, ethyl dibenzylaluminum, diethyl phenyl aluminum, diethyl p-tolyl aluminum, diethyl benzyl aluminum and other triorganoaluminum compounds. The preferred organoaluminum compounds are trialkylaluminums with aluminum triethyl being the most preferred.

The (B) component is also an organolithium compound. The term organolithium compound is meant to mean that the organo lithium compound corresponds to the formula R-Li in which R is a monovalent hydrocarbon radical with 1 to 20 carbon atoms, especially n-butyllithium, secondary butyllithium, hexyllithium and methyllithium are representative thereof. Of these, butyllithium is the preferred lithium compound.

The (C) component of the catalyst of this invention is pyridine. No special attention is needed to describe the pyridine except to say that the pyridine used should not contain any impurity or impurities that would have an adverse effect on the hydrogenation of the dicyclopentadiene.

The reaction temperature of the hydrogenations may be conducted from 0° C. but a more preferred range is from 30° C. to 70° C.

No upper limit on the hydrogen pressure has been determined but a preferred range is from 50 to 600 pounds per square inch gauge of hydrogen.

The hydrogenations of this invention are usually conducted in an inert solvent. Any inert aromatic or aliphatic solvents may be employed to dissolve the catalyst components and the cyclopentadiene. These include pentane, cyclopentane, n-octane and toluene. The volume ratio of cyclopentadiene to solvent may vary from about 1/1 to about 200/1. Cyclopentane is the preferred solvent.

The mole ratio of the catalyst component to each other is important in obtaining the improved hydrogenation rates when one hydrogenates cyclopentadiene to form cyclopentene. The mole ratio of the trialkylaluminum compound or organolithium to the soluble nickel compound must be within a range of from 7/1 to 11/1 to obtain improved hydrogenation rates over those disclosed in German Pat. No. 2,327,230. As noted in the German Patent, the mole ratio of the pyridine to the nickel compound should be within the range of 1/1 to 2.5/1, with a more preferred ratio of about 2/1.

The practice of this invention is further illustrated by reference to the following examples which are intended to be representative rather than restrictive of the scope of the invention. Unless otherwise indicated, all parts and percentages are by weight.

EXAMPLES

A typical procedure of the practice of the invention is employed wherein 1.3 millimoles (mm) of pyridine as a one molar solution in toluene are added to 0.65 mm of nickel octanoate as a 0.1 molar solution in toluene under nitrogen. After mixing these two materials for about 5 minutes, 4.55 mm of triethylaluminum as a two molar solution in toluene are added under nitrogen and the mixture stirred for at least two minutes. An amount of the catalyst mixture so as to give approximately 12,000 moles of cyclopentadiene per mole of nickel is transferred to a stirred autoclave containing one mole of cyclopentadiene. Hydrogen is then admitted at the desired pressure. Various aluminum/nickel mole ratios may be employed as well as various pyridine to nickel ratios all within the ratios set forth previously.

Various organolithium compounds may also be used as well as other trialkylaluminum or dialkylaluminum hydrides.

Using the procedure set forth above, a series of hydrogenations were conducted at varying mole ratios as indicated in the table below. The particular compounds employed were pyridine, n-octanoate and triethylaluminum. In these reactions, the hydrogenation was conducted at a a cyclopentadiene/nickel ratio of about 12,000/1, an initial hydrogen pressure of 435 psig, and the hydrogenation was conducted at 30° C.

Table 2

| Run No | Al/Ni | Mins | % Conv | % CPA | % CPE |
|---|---|---|---|---|---|
| 110 | 7 | 31 | 100 | 5.2 | 95 |
| 106 | 9 | 37 | 100 | 9.3 | 90.5 |
| 111 | 11 | 35 | 98 | 8.2 | 92 |
| 130* | 7 | 37 | 99 | 4.1 | 96 |

*CPD/Ni = 10,000, 250-400 psig $H_2$, 36°-39° C.
CPA = cyclopentane
CPE = cyclopentene It can be observed by comparing the data in Table 1 and Table 2 of this application that using aluminum/nickel mole ratios ranging from 1/1 up to 6/1 as set forth in Table 1 requires times of from about 72 to 150 minutes to reach a conversion of cyclopentadiene of 100 percent. On the other hand, in Table 2, utilizing an aluminum/nickel mole ratio of from 7/1 to 11/1, times ranging from 31 to about 37 minutes are required to arrive at a 100 percent conversion of cyclopentadiene.

COMPARATIVE EXAMPLE

In order to illustrate that the applicant's new range of Al/Ni gives unexpected results in the claimed range, the following experiment was conducted. Using the technique employed in the examples above and nickel octanoate/triethylaluminum/pyridine catalyst, a run was prepared utilizing triethylaluminum/nickel mole ratio of 6/1, a CPD/nickel mole ratio of 12,000/1, a hydrogen pressure of 435 psig, pyridine/nickel mole ratio of 2/1, and a temperature of 30° C. Results are as follows:

| Run No | Al/Ni | Mins | % Conv | % CPA | % CPE |
|---|---|---|---|---|---|
| 115 | 6 | 103 | 98 | 4.3 | 96 |

While certain representative embodiments and details have been shown for the purpose of illustrating the invention, it will be apparent to those skilled in this art that various changes and modifications may be made therein without departing from the spirit or scope of the invention.

What is claimed is:

1. In the process for selectively hydrogenating cyclopentadiene to form cyclopentene in the presence of a catalyst comprising (A) a hydrocarbon-soluble nickel compound selected from nickel salts of carboxylic acids and organo nickel compounds, (B) organo reducing agent corresponding to the formulae:

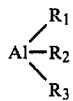

wherein $R_1$ is a monovalent hydrocarbon radical or hydrogen, and $R_2$ and $R_3$ are monovalent hydrocarbon radicals with 1 to 20 carbon atoms, and R-Li wherein R is a monovalent hydrocarbon radical with 1 to 20 carbon atoms and (C) pyridine, the improvement comprising employing the reducing agent, the soluble nickel compound and the pyridine in amounts wherein the mole ratio of aluminum or lithium to nickel ranges from 7/1 to 11/1, and the mole ratio of the pyridine to the nickel compound ranges from 1/1 to 2.5/1.

2. The process according to claim 1 in which the nickel compound is selected from the group of nickel 2-ethylhexanoate, nickel neodecanoate and nickel naphthenate, and wherein the organoaluminum compound is a trialkylaluminum.

3. The process according to claim 1 in which the nickel compound is selected from the group consisting of nickel, 2-ethyl hexanoate, nickel neodecanoate and nickel naphthenate and wherein the organoaluminum compound is butyllithium.

* * * * *